(12) United States Patent
Hall et al.

(10) Patent No.: US 7,710,000 B2
(45) Date of Patent: May 4, 2010

(54) EROSION AND WEAR RESISTANT SONOELECTROCHEMICAL PROBE

(75) Inventors: Clive E. Hall, Middlesex (GB); Li Jiang, Ridgefield, CT (US); Timothy G. J. Jones, Cottenham (GB); Andrew Meredith, Cambridge (GB); Nathan S. Lawrence, St. Neots (GB); Markus Pagels, Linton (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 170 days.

(21) Appl. No.: 11/499,332

(22) Filed: Aug. 4, 2006

(65) Prior Publication Data

US 2008/0028858 A1 Feb. 7, 2008

(51) Int. Cl.
*H01L 41/083* (2006.01)
*H01L 41/047* (2006.01)
(52) U.S. Cl. .................. 310/322; 310/334; 310/365; 310/366
(58) Field of Classification Search ............. 310/300, 310/322, 334, 323.12, 323.19, 363, 364
See application file for complete search history.

(56) References Cited

U.S. PATENT DOCUMENTS

| | | | |
|---|---|---|---|
| 4,216,671 | A | 8/1980 | Kurland |
| 4,956,149 | A | 9/1990 | Kawana et al. |
| 5,889,209 | A | 3/1999 | Piedrahita et al. |
| 6,426,974 | B2 | 7/2002 | Takahashi et al. |
| 6,437,326 | B1 | 8/2002 | Yamate et al. |
| 6,627,873 | B2 | 9/2003 | Tchakarov et al. |
| 6,880,402 | B1 | 4/2005 | Couet et al. |
| 6,886,406 | B1 | 5/2005 | Couet et al. |
| 6,995,360 | B2 | 2/2006 | Jones et al. |
| 7,407,566 | B2 * | 8/2008 | Jiang et al. ............ 204/400 |

(Continued)

FOREIGN PATENT DOCUMENTS

FR 2832703 A1 5/2003

(Continued)

OTHER PUBLICATIONS

Compton et al Electrode processes at the surfaces of sonotrodes Electrochimica Acta, vol. 41, No. 2, 1996, pp. 315-320.

(Continued)

*Primary Examiner*—Walter Benson
*Assistant Examiner*—Derek J Rosenau
(74) *Attorney, Agent, or Firm*—James McAleenan; Helene Raybaud; Brigid Laffey (57) ABSTRACT

The present invention, in one set of embodiments, provides methods and systems for integrating conducting diamond electrodes into a high power acoustic resonator. More specifically, but not by way of limitation, in certain embodiments of the present invention, diamond electrodes may be integrated into a high power acoustic resonator to provide a robust sensing device that may provide for acoustic cleaning of the electrodes and increasing the rate of mass transport to the diamond electrodes. The diamond electrodes may be used as working, reference or counter electrodes or a combination of two or more of such electrodes. In certain aspects, the high power acoustic resonator may include an acoustic horn for focusing acoustic energy and the diamond electrodes may be coupled with the acoustic horn.

32 Claims, 4 Drawing Sheets

U.S. PATENT DOCUMENTS

| | | |
|---|---|---|
| 2005/0029095 A1 | 2/2005 | Hall et al. |
| 2007/0126312 A1* | 6/2007 | Sung .......................... 310/306 |
| 2008/0157096 A1* | 7/2008 | Linares et al. ................. 257/77 |

FOREIGN PATENT DOCUMENTS

| | | |
|---|---|---|
| GB | 2 269 674 B | 10/1995 |
| GB | 2 336 668 B | 2/2003 |
| GB | 2 369 679 B | 4/2004 |
| GB | 2 369 680 B | 4/2004 |
| GB | 2 379 976 B | 2/2005 |
| GB | 2404738 A1 | 2/2005 |
| WO | 2004/003506 A2 | 1/2004 |
| WO | 2004/003506 A3 | 1/2004 |

OTHER PUBLICATIONS

Durant et al Sonoelectrochemistry: the effects of ultrasound on organic electrochemical reduction Electrochimica Acta, vol. 41, No. 2, 1996, pp. 277-284.

Reisse et al Sonoelectrochemistry in aqueous electrolyte: a new type of sonoelectroreactor Electrochimica Acta, vol. 39, No. 1, 1994, pp. 37-39.

Simm et al Sonically assisted electroanalytical detection of ultratrace arsenic Analytical Chemistry, vol. 76, 2004, pp. 5051-5055.

Windsor Scientific 'Sonotrode', Print out from Product Information, Aug. 17, 2006, www.windsorscientific.co.uk/DesktopDefault.aspx?tabindex=65&tabid=65.

Compton et al., "Sonoelectrochemical Processes: A Review", Electroanalysis 1997, pp. 509-522, vol. 9, No. 7.

Namgoong et al., "The effect of ultrasonic vibration on hard chromium plating in a modified self-regulating high speed bath", Thin Solid Films, 1984, pp. 153-159, vol. 120.

Kumar Sur et al., "Microwave Activation of Electrochemical Processes at Glass Carbon and Boron-Doped Diamond Electrodes", Electroanalysis 2005, pp. 385-391, vol. 17, No. 5-6.

* cited by examiner

EROSION AND WEAR RESISTANT SONOELECTROCHEMICAL PROBE

CROSS-REFERENCE TO RELATED APPLICATIONS

This application is related to U.S. application Ser. No. 11/499,329, filed on a date even herewith by Timothy G. J. Jones et al. and entitled "A High Power Acoustic Resonator with Integrated Optical Sensor Interface" the disclosure of which is incorporated herein by reference by Attorney all purposes. This application is also related to the following commonly-owned patents, U.S. Pat. No. 6,880,402 ("the '402 patent) to Couet et al., U.S. Pat. No. 6,886,406 ("the '406 patent) to Couet et al., and U.S. Pat. No. 6,995,360 ("the '360 patent") of which the entire disclosure of each is hereby incorporated by reference for all purposes.

BACKGROUND OF THE INVENTION

Combining high power ultrasound and electrochemical analysis functions and properties has most often previously been achieved by configuring a high power acoustic resonator and separate electrode system in a face-on geometry. In such an arrangement, the spacing between the electrode and acoustic resonator can be varied to vary the effect of the separated acoustic and electrode systems. However, it should be noted, that the spacing between the acoustic resonator and the electrode system in the face-on geometry will result in a decrease in the electrode cleaning capabilities of the acoustic resonator and the mass transfer rate associated with the electrode when operated contemporaneously with the acoustic resonator. Furthermore, investigations with regard to performance of such face-on configurations identified the existence of wear and erosion issues associated with the systems In another arrangement configured to provide for combined ultrasound and electrochemical analysis functions and properties, an acoustic horn of a high power acoustic resonator has itself been used as an electrode. In these configurations, the acoustic horn itself is used as the working electrode in an electrochemical circuit. J. Reisse et al. in an article entitled "SONOELECTROCHEMISTRY IN AQUEOUS ELECTROLYTE: A NEW TYPE OF SONOELECTROREACTOR", *Electrochim. Acta*, 39, 37-39 (1994), disclose using a titanium ultrasonic horn as a working electrode to provide for depositing copper from a solution of copper sulphate in the presence of high power ultrasound at a frequency of 20 kHz. Durant et al. describe using a titanium horn as the working electrode to study the effects of high power ultrasound on the electrochemical reduction of benzaldehyde and benzoquinone. (Durant, A., François, H., Reisse, J. and Kirsch-de Mesmaeker, A., "SONO-ELECTROCHEMISTRY: THE EFFECTS OF ULTRASOUND ON ORGANIC ELECTROCHEMICAL REDUCTION", *Electrochim. Acta*, 41, 277-284 (1996).

Other arrangements provide for attaching the electrode to an acoustic horn. Such an arrangement may be termed a sonotrode and such a device is available commercially from Windsor Scientific. The Windsor Scientific sonotrode consists of a glassy carbon disk electrode set in the end of a quartz rod, wherein the quartz rod is screwed into the end of an ultrasonic horn. Although the sonotrode is a combined system with the acoustic resonator and electrode combined, the electrode is still disposed distally from the acoustic horn; so as with the face-on geometry, the separation will result in a decrease in the electrode cleaning capabilities of the acoustic resonator and the mass transfer rate associated with the electrode when operated contemporaneously with the acoustic resonator. Further, the Windsor Scientific sonotrode does not provide a rugged and wear/erosion resistant design and may not be capable of operating at high acoustic powers and/or may experience degradation of the glassy carbon disk electrode under acoustic functions. In another sonotrode-type device, A. O., Simm et al. "SONICALLY ASSISTED ELECTROANALYTICAL DETECTION OF ULTRATRACE ARSENIC", *Anal. Chem.*, 76, 5051-5055 (2004), an electrode may be attached to a small permanent magnet that may be made to vibrate by passing current through an adjacent electric coil.

In a further acoustic resonator and electrode arrangement, modifying the idea of using the acoustic horn as the electrode, a platinum electrode is disclosed that is bonded into a hole drilled in the titanium tip of an acoustic horn using an adhesive. (R. G. Compton, et al., "ELECTRODE PROCESSES AT THE SURFACE OF SONOTRODES", *Electrochim. Acta*, 41, 315-320 (1996)). In such an arrangement, as with arrangements wherein the acoustic horn acts as an electrode, the distance between the electrode and the acoustic horn does not become an issue. In the electro-acoustic system disclosed by Compton, electrical connections to the platinum electrode are provided by wire connections passing through the side of the acoustic horn to the platinum electrode. While the reference provides a sonotrode that effectively addresses issues regarding separation of the acoustic resonator and the electrode it does not address using acoustic energy to clean the electrode or provide for effectively configuring the acoustic resonator and electrode system for combined operation. Furthermore, the reference does not disclose a sonotrode that may be suited for remote operation, operation in harsh environments—including high temperatures or pressures—or that can be effectively used repeatedly at high acoustic energy levels.

BRIEF SUMMARY OF THE INVENTION

Embodiments of the present invention relate to integrating an electrode system with a high power acoustic resonator. More specifically, but not by way of limitation, embodiments of the present invention provide for integrating a diamond electrode with the high power acoustic resonator to provide a sonoelectrochemical interface that is erosion and wear resistant that may be used in fouling and harsh environments and is capable of remote operation. Additionally, in certain embodiments of the present invention, by integrating the electrode system into an acoustic horn of the acoustic resonator the system may provide for effective cleaning of the electrode and effective operation of the sonoelectrochemical interface at high acoustic energies.

In one embodiment, an erosion and wear resistant sonoelectrochemical probe configured for high power ultrasonic operation is provided comprising a high power acoustic resonator with an acoustic body and a transducer coupled to the base of the acoustic body, a diamond electrode coupled with a tip of the acoustic body and an electrically conducting element coupled with the diamond electrode. In one aspect of the invention, the diamond electrode may be a diamond microelectrode array. In certain aspects, the electrically conducting element may be disposed within the acoustic body so that it passes from the tip of the acoustic body and through the base of the acoustic body. Disposing the electrically conducting element inside the acoustic body may provide for a sonoelectrochemical probe that may be used in extreme conditions and/or for effective operation of the acoustic resonator at high powers with the combined electrode system.

The diamond electrode may comprise a boron-doped diamond. In certain aspects, the boron-doped diamond electrode may be configured so that there is a central disc of boron-doped diamond surrounded by a concentric ring of non-conducting diamond, wherein the concentric ring of electrically non-conducting diamond provides for the insulation of the central disc of the boron-doped diamond from the acoustic body. In further embodiments of the present invention, the diamond electrode may comprise a macroscopic and/or a microscopic array formed from boron-doped diamond regions and electrically non-conducting diamond regions. In certain aspects, the boron-doped diamond regions and electrically non-conducting diamond regions may be arranged in concentric rings around a central disc of boron-doped diamond. In the array and ring-type configurations of the non-conducting and electrically conducting diamond, the individual electrodes of the sonoelectrochemical probe formed by the electrically isolated regions of the electrically conducting diamond may be configured to provide working, counter and reference electrodes. In such configurations, the sonoelectrochemical probe may comprise a complete and robust, integrated system for performing sonoelectrochemistry measurements.

In an embodiment of the present invention, the rugged and wear resistant sonoelectrochemical probe may be contacted with a substance or the substance may be made to contact the sonoelectrochemical probe, a second electrode may also be contacted with the substance, the high power acoustic resonator may be used to generate acoustic energy and electrical properties of an electrical current flowing between sonoelectrochemical probe and the second electrode may be measured. Further, a third electrode may also be contacted with the substance. The second electrode may be coupled with the sonoelectrochemical probe to provide an integrated system for taking sonoelectrochemical measurements. Yet further, the third electrode may be coupled with the sonoelectrochemical probe and the second electrode to provide a three electrode integrated system for taking sonoelectrochemical measurement using the working, reference and counter electrode system well know to those skilled in the art. In other aspects, multiple electrodes may be formed on the active face of the sonoelectrochemical probe by the creation of regions of electrically conducting diamond on the electrode surface of the sonoelectrochemical probe, electrically insulated from each other. In certain aspects, these electrically isolated regions may be areas of electrically conducting diamond surrounded by non-conducting diamond, and these multiple electrodes may be used as working and reference electrodes and/or counter electrodes. In certain aspects, the high power acoustic resonator may be used to generate acoustic energy to clean the sonoelectrochemical probe and/or to mix the substance or substances in contact with the sonoelectrochemical probe.

Further areas of applicability of the present invention will become apparent from the detailed description provided hereinafter. It should be understood that the detailed description and specific examples, while indicating various embodiments of the invention, are intended for purposes of illustration only and are not intended to limit the scope of the invention.

BRIEF DESCRIPTION OF THE DRAWINGS

In the figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

The present invention will become more fully understood from the detailed description and the accompanying drawings, wherein.

DETAILED DESCRIPTION OF THE INVENTION

The ensuing description provides preferred exemplary embodiment(s) only, and is not intended to limit the scope, applicability or configuration of the invention. Rather, the ensuing description of the preferred exemplary embodiment(s) will provide those skilled in the art with an enabling description for implementing a preferred exemplary embodiment of the invention. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments maybe practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Interest in the combination of high power ultrasound and electrochemical analysis has developed based upon an understanding of the advantages of using high power ultrasound when making electrochemical measurements and the term sonoelectrochemistry has been coined to describe the union of high power ultrasound and electrochemical measurements. In particular, two advantages have been observed in the use of high power ultrasound with electrochemical measurements.

With regard to the first advantage, it has been found that the use of ultrasound significantly increases the rates of mass transport to and from an electrode and, thus, causes an increase in the measured electrical current. This increase is caused by an increase in the flow of electrolyte solution past the working electrode, which is caused by acoustic cavitation and/or acoustic streaming. This gives rise to what is essentially hydrodynamic control of mass transport.

In a sonoelectrochemical system comprising an electrode-type electrochemical system and an acoustic system, the steady state limiting current ($I_{lim}$) may be described by equation (1):

$$I_{lim} = \frac{nFACD}{\delta} \qquad [1]$$

where n is the number of electrons involved in the electrochemical reaction, F is the Faraday constant, A is the area of the electrode, C is the concentration of the electroactive species in bulk solution, D is the diffusion coefficient of the electroactive species in the solution and $\delta$ is the thickness of the stagnant diffusion layer between the electrode and the bulk electrolyte solution. In experiments, values of $\delta$ of one µm have been reported, which are considerably smaller than values achieved under quiescent conditions. From experimentation and analysis, some researchers have found that equation [1] may be expressed as:

$$I_{lim} = nFACm_i \qquad [2]$$

where $m_i$ is the average mass transport coefficient. In these experiments, the researchers commented that mass transport rates achieved by the application of high power ultrasound can be 100-1000 times greater than with other hydrodynamic methods. For example, it has been noted that a value of $m_i$=0.0643 cm/s, which may be obtained by sonication in a system comprising a combination of an ultrasound source and an electrode system, could only be achieved by laminar flow in a rotating disk electrode at a rotation speed of greater than 160,000 rpm, a value that is not practically attainable.

The second advantage of the sonoelectrochemical system is that the process of acoustic cavitation, namely the violent expansion and collapse of gas bubbles within one acoustic cycle, can clean the electrode surface and prevent passivation. The cleaning and erosion of solid surfaces by high power ultrasound is often termed cavitational erosion. The prevention or reduction of electrode fouling by the use of high power ultrasound has enabled electrochemical measurements to be applied to the analysis of a wide range of complex samples that would otherwise require extensive sample preparation prior to the analysis. Sonoelectrochemical measurements have been applied to a number of complex and potentially fouling systems, including manganese in tea, copper in whole blood, copper in beer, lead in human saliva, nitrite in eggs and the detection of lead in water following extraction into an organic phase.

A critical aspect of sonoelectrochemical measurements is the relative positioning of the acoustic horn that generates the high power ultrasound and the working electrode. In general, up until now, the commonest configuration has been to position the acoustic generator and the working electrode face on with a separation of typically 1-30 mm. This configuration is cumbersome and small variations in the relative positioning of the acoustic generator and working electrode can lead to variations of up to factors of 15 in the measured currents. Consequently, the accurate positioning of the acoustic generator relative to the working electrode is essential for the determination of limiting currents.

In a high power acoustic resonator, an acoustic horn may be used to generate high power ultrasound. The high power acoustic resonator may comprise an acoustic or ultrasonic (the words may be used interchangeably herein) body, which may be referred to as an acoustic horn, which is a mechanical device for amplifying the displacement and means of generating a sinusoidal displacement—such as a piezoelectric or magnetostrictive element. The displacement is generated by several piezoelectric elements and the amplification of the displacement is achieved by the reduction in cross-sectional area along the length of the horn, which is typically made of a metal such as steel or titanium.

Figure 1:
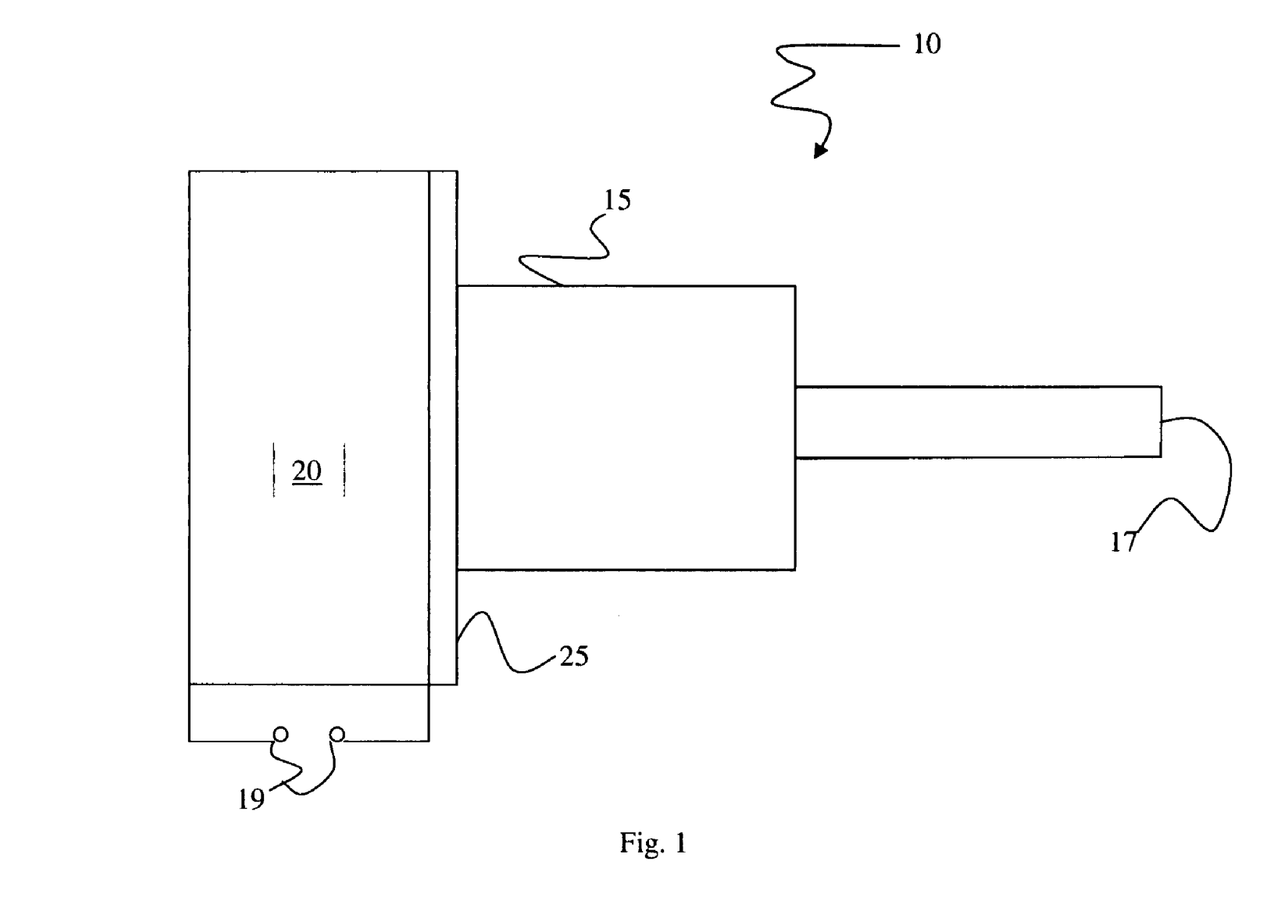
FIG. 1 is a schematic type illustration of a high power acoustic resonator that may be used in an embodiment of the present invention.

FIG. 1 shows a schematic of a high power acoustic resonator that may be used in an embodiment of the present invention. Generally, a high power acoustic resonator 10 may comprise an acoustic body/acoustic horn 15 (the terms acoustic body and acoustic horn may be used interchangeably herein) attached to and/or incorporating an ultrasonic transducer 20. In certain aspects, the ultrasonic transducer 20 may be disposed within or coupled to a base 25 of the acoustic horn 15. A power source 19 may be coupled with the ultrasonic transducer 20 to provide power to the ultrasonic transducer 20. In an embodiment of the present invention, a high power acoustic resonator with integrated electrode system may consist of an ultrasonic piezoelectric transducer coupled to a suitable metal horn.

In one aspect of such an embodiment, the piezoelectric transducer may be configured to operate in a longitudinal mode. In such an aspect, the resulting ultrasonic device may be characterized by having a sharp resonant frequency, which can be conveniently determined by the measurement of the admittance (or impedance) spectrum of the device. Furthermore, the resonance frequency of the appropriate longitudinal mode of such a device is sensitive to any solid deposit that forms on the tip of the horn and the magnitude of the frequency shift is a measure of the mass loading. The high power acoustic resonator 10 may comprise an ultrasonic piezoelectric transducer coupled to a suitable metal horn and may operate in the frequency range 10-250 kHz and may deliver high levels of acoustic power, typically in the range 1-500 W, when driven by a high input alternating voltage at its resonant frequency.

The acoustic horn may oscillate laterally or may be configured to oscillate in a longitudinal mode. The resonant frequency of the acoustic device operating in a longitudinal mode is determined by the thickness of the piezoelectric, the acoustic horn 15 and the materials from which the piezoelectric and acoustic horn 15 are constructed. The acoustic horn 15 may have a stepwise tapering design, an exponentially reducing diameter or the like. The acoustic horn 15 may be made of titanium and have a sharp resonant frequency in air of 40 kHz, where the area of the horn tip is of the order 0.2 cm². In some acoustic horn 15 designs, the tapering is degenerated to a single step giving the acoustic horn 15 a pin-like shape. Other horn shapes can be envisaged, including the case where its thickness is very much less than the wavelength of sound and the horn is a thin layer of material, for example but not by way of limitation, that couples the ultrasonic transducer to the borehole fluids and their deposits.

Acoustic horns are devices for generating high power ultrasound. An acoustic (or ultrasonic) horn may consist of a means of generating a sinusoidal displacement, such as a piezoelectric or magnetostrictive element, and a mechanical device for amplifying the displacement. The displacement of the acoustic horn may be generated by several piezoelectric elements and the amplification of the displacement is achieved by the reduction in cross-sectional area along the length of the horn, which is typically made of a metal such as steel or titanium. The horn is designed such that an anti-node is located at the tip of the horn where the displacement is a maximum. When ultrasonic horns are operated at high power levels, typically in excess of 10 W, the amplitude of the displacement of the tip may be several tens of microns. Operation of the ultrasonic horn at high power when the tip of the horn is immersed in liquids at ambient pressure will give rise to acoustic cavitation in the liquid and the flow of liquid away from the tip by a phenomenon known as acoustic streaming. Acoustic cavitation in water at ambient pressure is achieved at a power density in excess of 0.5-1.0 W per square centimeter of horn tip and at a frequency of 20 kHz. In some embodiments of the present invention, the acoustic horn 15 may comprise a base end 25 that may provide a contact with the ultrasonic transducer 20 to provide for the ultrasonic transducer 20 to vibrate the acoustic horn 15.

The resonant frequency of the acoustic device operating in a longitudinal mode may be determined by the size of the ultrasonic transducer 20 and the acoustic horn 15 and the materials from which the ultrasonic transducer 20 and the acoustic horn 15 are constructed. The design of the acoustic horn 15 may vary and may be a stepwise tapering, a smooth tapering with an exponentially reducing diameter or the like. The acoustic horn 15 may be designed such that the tapering is degenerated to a single step giving the acoustic horn 15 a pin-like shape. Other horn shapes can be envisaged, including the case where its thickness is very much less than the wavelength of sound and the horn is a thin layer of material that is coupled to the ultrasonic transducer 20. In embodiments of the present invention, the design of the acoustic horn 15 may be such as to amplify the acoustic energy onto the tip of the horn 17. In certain aspects of the present invention, the acoustic horn 15 may be made of titanium. Additionally, in certain aspects, the area of the horn tip 17 may be of the order of 0.2-2.0 $cm^2$. In some embodiments of the present invention, the length of the acoustic horn 15 is an odd integer multiple N of half the wavelength ($\lambda/2$) of the acoustic wave generated by the ultrasonic transducer 20.

Figure 2:
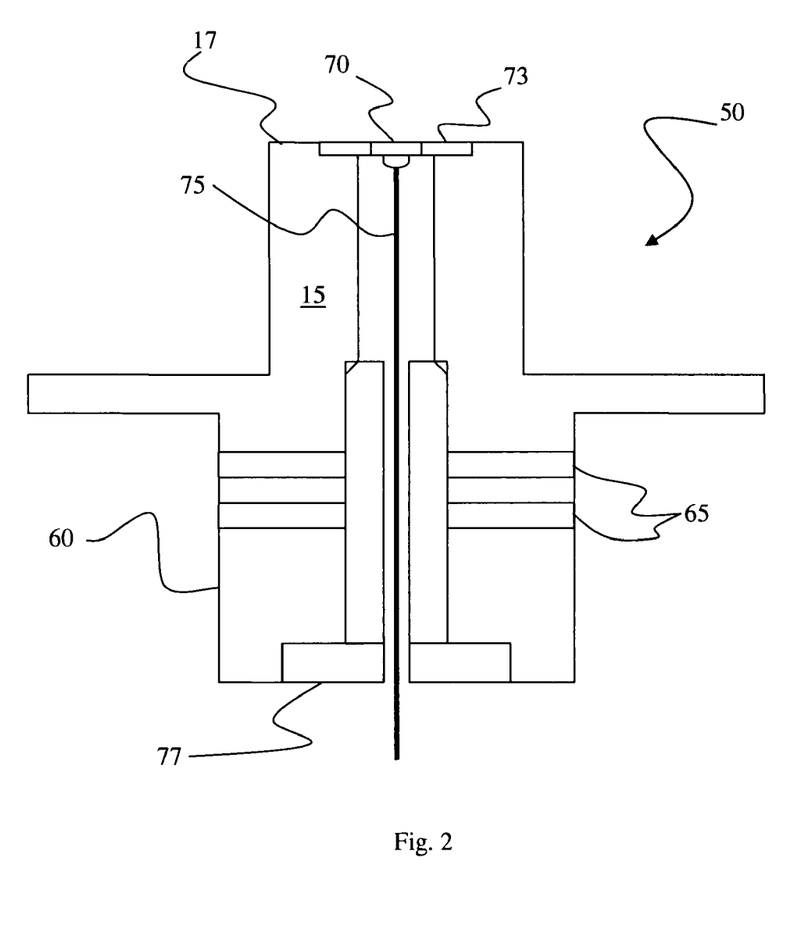
FIG. 2 is a schematic-type diagram illustrating a high power acoustic resonator with an integrated electrically conducting diamond electrode, in accordance with an embodiment of the present invention.

FIG. 2 is a schematic-type diagram illustrating a high power acoustic resonator with an integrated electrically conducting diamond electrode, in accordance with an embodiment of the present invention. In the depicted embodiment, a high power acoustic resonator with an integrated electrically conducting diamond electrode 50 is illustrated. The high power acoustic resonator with an integrated electrically conducting diamond electrode 50 may comprise an acoustic horn 15, a base 60 and a transducer 65. In certain aspects, the transducer 65 may be integrated into the base 60 and in other aspects; the transducer 65 may be coupled with the base 60.

In an embodiment of the present invention, the high power acoustic resonator with an integrated electrically conducting diamond electrode 50 may comprise an electrically conducting diamond electrode 70 disposed at a tip 17 of the acoustic horn 15. In certain aspects, the single electrically conducting diamond electrode 70 may comprise boron-doped diamond. In the illustrated embodiment, the electrically conducting diamond electrode 70 may be electrically isolated from the acoustic horn 15 by an isolating element 73. In certain aspects, the isolating element 73 may comprise non-conducting diamond.

In an embodiment of the present invention, a diamond substrate may be located at the tip 17 of the acoustic horn 15, wherein the diamond substrate may be of the order of about 1-10 millimeters in diameter and comprise a ring of electrically non-conducting diamond with a central disc approximately 0.5-5.0 millimeters wide of boron-doped diamond. This diamond substrate may be formed by taking a diamond substrate and doping a central region with boron.

The conductive diamond in the diamond substrate may be fabricated by any method known to the art, but is preferably fabricated by doping during growths and more preferably by doping with boron during growth. An alternative method of creating the conductive diamond region or regions is to use ion implantation. Alternative dopants may include other substances capable of making the diamond substrate electrically conducting.

An electrically conducting element 75, such as a copper or a silver wire may be coupled with the electrically conducting diamond electrode 70. In alternative embodiments, the electrically conducting element 75 may comprise an electrically conducting channel or the like. In certain aspects, the electrically conducting element 75 may be brazed to the back of the electrically conducting diamond electrode using, for example, a copper/silver/titanium active braze (e.g., EL-91 braze, made by Drijfbout BV), which consists of a eutectic copper/silver wire (72 weight percent silver) with a titanium core that constitutes approximately 10 weight percent of the wire.

Merely by way of example, to provide for soldering/brazing using a non-active solder/braze of the electrically conducting element 75 to the electrically conducting diamond electrode 70, the back of the electrically conducting diamond electrode 70 may be coated with a mixture of elements such that they bond to diamond and yield a solderable/brazeable surface. Merely by way of example, a method using radio-frequency ("RF") bias sputtering may be employed to sputter sequentially titanium, platinum and gold layers (approximately 0.1, 0.2 and 1.0 µm in thickness, respectively) onto the back of the electrically conducting diamond electrode 70 using a mechanical masking technique. The edge and rim of the isolating element 73 may also be coated with the same titanium, platinum and gold layers by modifying the mechanical mask to facilitate the mounting of the diamond electrode into the recess in the tip of the acoustic horn 17, noting that the geometries of the two metal layers must not generate any electrical contact between the ultrasonic horn body 15 and the electrically conducting element 75 either after sputter coating or after bonding the isolating element 73 into the ultrasonic horn body 15. The tip of the ultrasonic horn 17 may also be coated with the same titanium, platinum and gold layers to facilitate the brazing/soldering of isolating element 73.

In some methods of constructing the sonoelectrochemical probe, the electrically conducting diamond electrode 70 and/or the isolating element 73 may be soldered into a recess that may be created/machined into the tip of acoustic horn 17. In such construction methods, the solder used may have a lower melting point than the braze used to attach electrically conducting element 75 to the electrically conducting diamond electrode 70. Merely by way of example, such braze may comprise the gold-germanium eutectic, which consists of gold and germanium in the mole fraction ratio of 0.88:0.12 and has a melting point of around 365 degrees Centigrade. Care must be taken during such soldering to ensure that there is no electrical short circuit created between the electrically conducting diamond electrode and the acoustic horn 15. The electrically conducting element 75 may be insulated from the acoustic horn 15 by surrounding the electrically conducting element 75 with non-conducting tubing.

In one embodiment of the present invention, a central bolt 77 may be disposed in or coupled with the base 60. The central bolt 77 may act to provide access into an interior volume of the acoustic horn 15, provide access to the back of the electrically conducting diamond electrode 70, provide an anchoring point for the high power acoustic resonator with an integrated electrically conducting diamond electrode 70, provide stability for the high power acoustic resonator with an integrated electrically conducting diamond electrode 70, and/ or the like. In certain aspects, the electrically conducting element 75 may be brought to the interior/back of the acoustic horn 15 through a hole in the central bolt 77. Further, such integration in these embodiments may provide for a self-contained high power acoustic resonator with the integrated electrically conducting diamond electrode that may be suitable for use in harsh conditions and/or for remote operations.

An alternative electrical connection to the electrically conducting diamond electrode 70 may be made using wire bonding, which is a technique much used in the integrated circuits industry. Implementation of the wire bonding technique may require the backside (the side that may be accessed from the interior of the acoustic horn 15) of the electrically conducting diamond electrode 70 to be coated with a mixture of elements chosen such that they bond to diamond and give a wire-bondable surface. One such combination of elements, for example, is achieved by layers of titanium, platinum and gold (0.1, 0.2 and 1.0 μm in thickness, respectively), which may be applied by sequential RF bias sputtering using photolithographical techniques. Again, care must be taken that the pattern coating is such a size and shape that there is no electrical short circuit between the electrically conducting diamond electrode 70 and the acoustic horn 15 either before or after bonding the isolating element 73 into the ultrasonic horn body 15.

Figure 3:
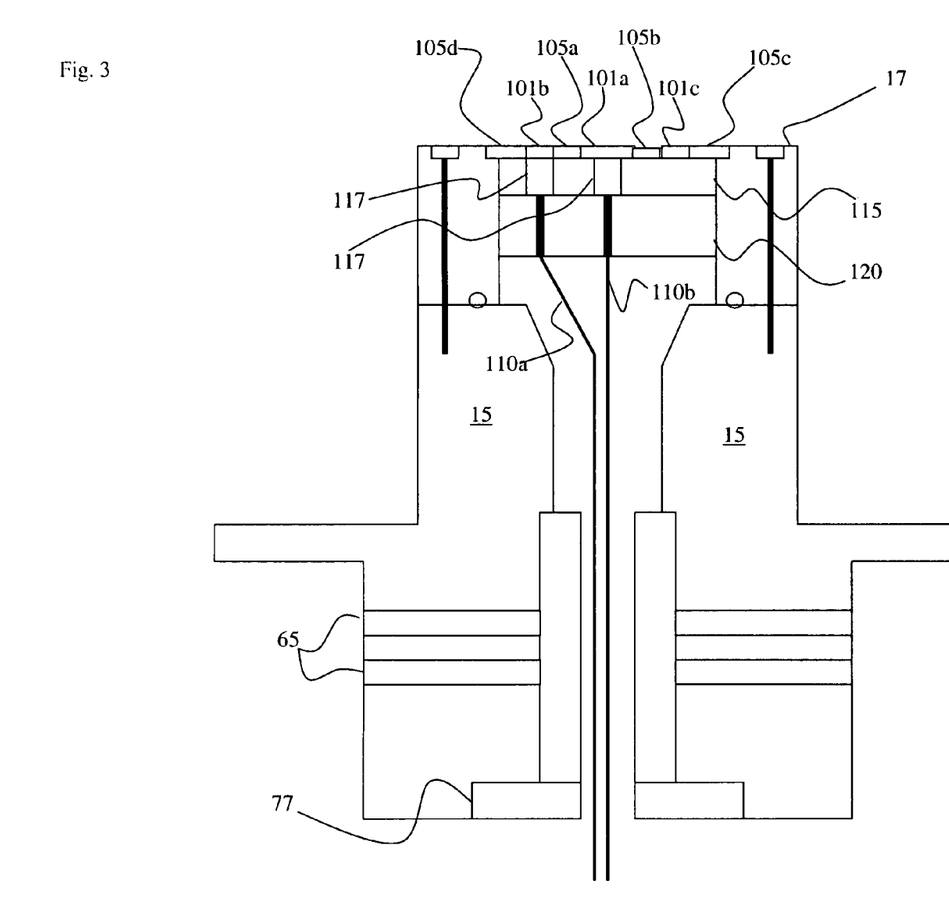
FIG. 3 is a schematic-type diagram illustrating a high power acoustic resonator with an integrated diamond electrode comprising a plurality of conducting regions separated by non-conducting regions that may be used as reference or counter electrodes and working electrodes, in accordance with an embodiment of the present invention.

FIG. 3 is a schematic-type diagram illustrating a high power acoustic resonator with an integrated diamond electrode comprising a plurality of conducting regions separated by non-conducting regions that may be used as reference and/or counter and working electrodes, in accordance with an embodiment of the present invention. In certain embodiments of the present invention, the conducting-diamond electrode may comprise a plurality of electrically conducting diamond electrodes, illustrated in FIG. 3 as the electrically conducting diamond electrodes 101a, 101b and 101c, disposed in the tip 17 of the acoustic horn 15 with at least one of the electrically conducting diamond electrodes 101a, 101b and 101c being electrically isolated from the acoustic horn 15. In such embodiments, one or more of the electrically conducting diamond electrodes 101a, 101b and 101c may comprise boron-doped diamond. In certain aspects, the acoustic horn 15 may comprise titanium.

In one embodiments of the present invention, the electrically conducting diamond electrodes 101a, 101b and 101c may be arranged such that the electrically conducting diamond electrodes 101a, 101b and 101c and the tip 17 of the acoustic horn 15 are coplanar. In an alternative embodiment, the electrically conducting diamond electrodes 101a, 101b and 101c may be disposed proximal to the tip 17. Such precise positioning of the electrically conducting diamond electrodes 101a, 101b and 101c relative to the tip illustrates one of the advantages of incorporating the conductive elements and other interfaces between the electrically conducting diamond electrodes 101a, 101b and 101c and elements external to the sonoelectrochemical probe within the acoustic horn.

In the illustrated embodiment, the electrically conducting diamond electrode 101a may comprise a disc surrounded by an electrically insulating region 105a and 105b, where insulating regions 105a and 105b may comprise a single ring of non-conducting material surrounding the electrically conducting diamond electrode 101a. Similarly, electrically conducting diamond electrodes 101b and 101c may comprise a single ring of electrically conducting diamond and electrically insulating regions 105c and 105d may comprise a single ring of electrically insulating material. In certain aspects, the electrically conducting diamond electrodes 101a, 101b and 101c may comprise boron-doped diamond and the electrically insulating regions 105a, 105b, 105c and 105d may comprise undoped diamond. In a further embodiment, the number of electrically conducting diamond and electrically insulating diamond rings may be increased so long as the last diamond ring is electrically insulating.

Merely by way of example, in a sonoelectrochemical probe in accordance with one embodiment of the present invention, a diamond substrate may be located at the tip 17 and this substrate may have a diameter of approximately 9 mm. This substrate may comprise a 2 mm diameter central electrically conducting diamond electrode, which may be used as a working electrode, and may be surrounded by concentric rings of electrically non-conducting diamond alternating with concentric rings of electrically conducting diamond. Since diamond is itself a non-conducting substance, the concentric rings of electrically non-conducting diamond may comprise diamond. The electrically conducting diamond rings may comprise doped diamond where the dopant may be boron, phosphorus, sulfur or the like, or any other dopant providing for electrical conduction by the doped diamond. The concentric rings of the electrically conducting diamond may have widths of the order of about 1-2 millimeters and, the concentric rings of the electrically non-conducting diamond may have widths of the order of 1-2 millimeters. In certain aspects, one of the concentric rings of the electrically conducting diamond, which is electrically insulated by the surrounding rings of non-conducting diamond, may function as a counter electrode or a reference electrode in an electrochemical circuit. In further aspects another electrically conducting diamond ring, which is electrically insulated by the surrounding rings of electrically non-conducting diamond, may function as another reference electrode or counter electrode.

In an embodiment of the present invention, electrical contact with one or more of the electrically conducting diamond electrodes 101a, 101b and 101c may be made using electrically-conducting channels 117 that are located in an insulating channel-support-matrix 115. In certain aspects, the electrically conducting channels 117 and the insulating channel-support-matrix 115 may comprise a drilled, solder-filled PCB board or a laser drilled electrically non-conducting diamond plate filled with an active metal braze. Merely by way of example, the electrically-conducting channels 117 may have diameters of the order of fractions of millimeters and the electrically-conducting channels 117 may comprise channels in the insulating channel-support-matrix 115 that may be filled with a mixture of copper, silver and titanium braze or the like. The electrically conducting channels 117 may be positioned such that one or more of the electrically conducting channels 117 is in contact with one of the electrically conducting diamond electrodes 101a, 101b or 101c.

A plate may be used to help position and/or provide structural support to the insulating channel-support-matrix 115 and diamond electrode. In certain aspects, the plate 120 may comprise ceramic, plastic or the like. The insulating channel-support-matrix 115 and the electrically conducting channels 117 may be held in contact with the underside of the electrode array, where the electrode array comprises the electrically conducting diamond electrodes 101a, 101b or 101c and the electrically insulating regions 105a, 105b, 105c and 105d, by a mechanical support 120. The mechanical support 120 may include one or more holes through which electrically conducting elements or channels 110a and 110b may pass and make contact with the electrically conducting channels 117. The electrically conducting elements or channels 110a and 110b must not make electrical contact with the mechanical support 120 should the mechanical support 120 be made of an electrically conducting material such as a metal.

In certain aspects, the electrically conducting elements or channels 110a and 110b may be soldered or wire bonded to the electrically conducting diamond electrodes 101a, 101b or 101c. Further, in certain aspects, electrically conducting elements or channels 110a and 110b may pass through and out of the acoustic horn 15 through a hole in the central bolt 77 or the like. The electrically conducting elements or channels 110a and 110b may be connected to electrical sources, processors and/or the like to provide for operation and or analysis of one or more of the electrically conducting diamond electrodes 101a, 101b or 101c. In one embodiment of the present invention, the insulating channel-support-matrix 115 and the mechanical support 120 may be machined to provide that the insulating channel-support-matrix 115 and the mechanical support 120 key mechanically into each other. In this way, the orientation of the electrically conducting channels 117 and the one or more holes in the mechanical support 120 may be maintained during assembly.

In one embodiment of the present invention, a top surface of the insulating channel-support-matrix 115 may be patterned with a metal layer to provide for electrical contact to the underside of the one or more electrically conducting diamond electrodes 101a, 101b or 101c, such metal layer may comprise: (a) a standard copper layer, such as is used on a PCB board, and may be applied to the insulating channel-support-matrix 115 using standard PCB patterning and etch techniques; (b) sequential layers of titanium, platinum and gold and these layers may be applied to the insulating channel-support-matrix 115 by RF bias sputtering using a mechanical or photolithographical mask. Further, in some embodiments of the present invention, the bottom surfaces of the electrically conducting diamond electrodes 101a, 101b or 101c may be sequentially RF bias sputtered with titanium, platinum and gold layers using a mechanical or lithographic mask to provide that the pattern produced by the sputtering matches the metal layer pattern on the insulating channel-support-matrix 115.

In certain fabrication methods, the acoustic horn 15 may comprise two parts to allow for the electrode system to be assembled and the two parts may be affixed together after the electrode system has been be assembled. Affixation of the two parts may be provided by screws, bolts, gluing, soldering, welding and/or the like.

In certain embodiments of the present invention, the one or more of the electrically conducting diamond electrodes 101a, 101b or 101c provided as a counter electrode may be configured in the electrical arrangement to act as a second working electrode. In such embodiments, an external counter may be utilized with the sonoelectrochemical probe. Such configurations may provide for obtaining information about either the electrochemical processes occurring at the working electrode(s) and/or the flow of species across the electrically conducting diamond electrodes 101a, 101b or 101c.

Figure 4:
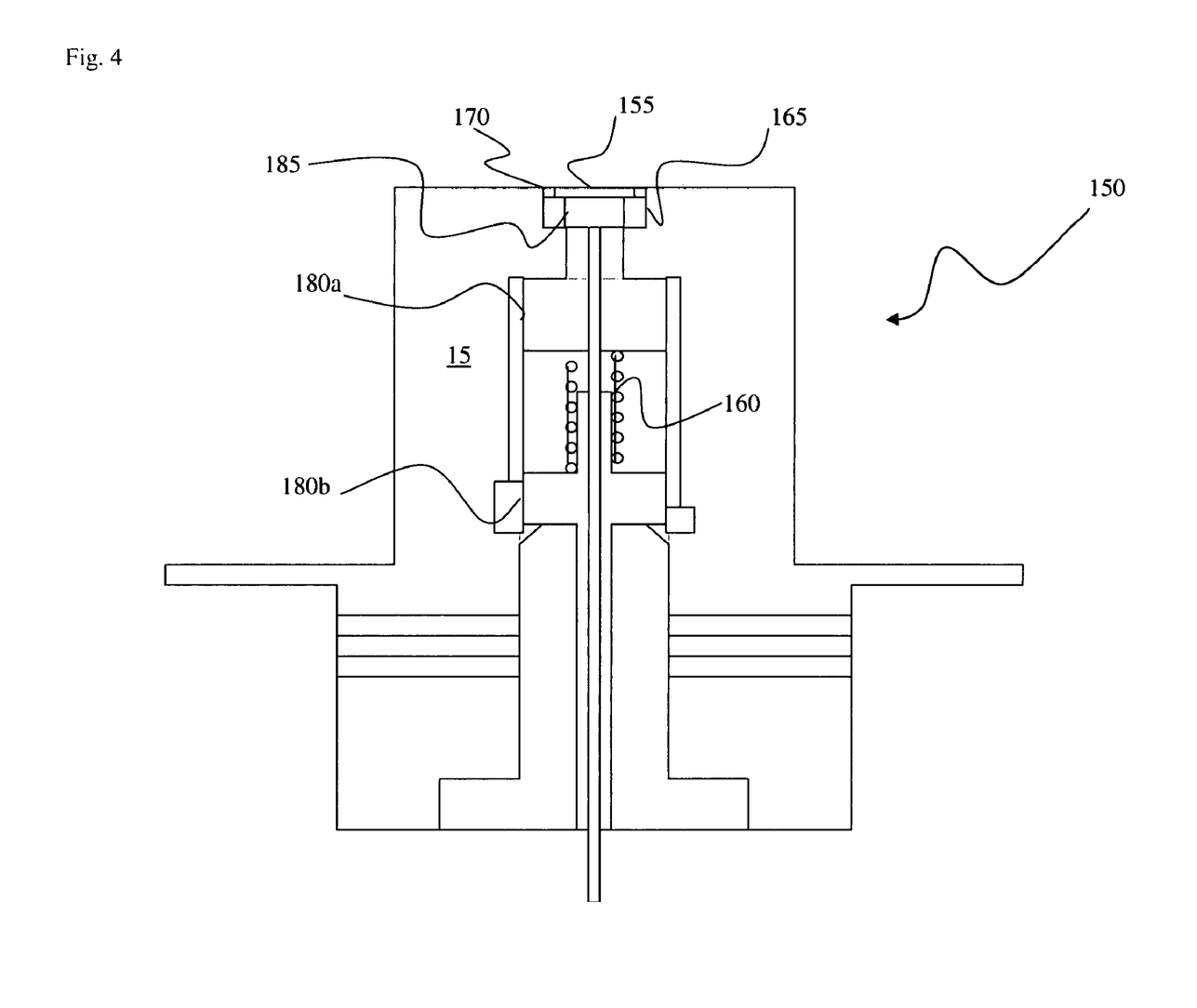
FIG. 4 is a schematic-type diagram illustrating a high power acoustic resonator with an integrated diamond electrode array, in accordance with an embodiment of the present invention.

FIG. 4 is a schematic-type diagram illustrating a high power acoustic resonator with an integrated diamond electrode array, in accordance with an embodiment of the present invention. In certain aspects, the illustrated sonoelectrochemical probe 150 comprises a diamond electrode array 155. The diamond electrode array 155 may comprise a substrate across which may be an array of conducting and non-conducting regions. In one aspect of the present invention, the substrate may comprise diamond, the conducting regions may comprise doped diamond regions and the non-conducting regions may comprise diamond. In such embodiments, the doped diamond regions may be doped with a dopant such as boron, phosphorous, sulfur, arsenic or the like. The diamond electrode array 155 may be a macro-array and/or a micro-array.

Similar to the embodiment described in FIG. 3, the diamond electrode array 155 may be supported by a non-conducting support layer (not shown) through which conducting channels and/or elements may provide electrical contact with the conducting regions of the diamond electrode array 155. In some aspects of the present invention, a sapphire ring 165 may be brazed into a recess in the acoustic horn 15 using techniques that may be appreciated by those of skilled in the art. In such aspects, a portion of a top surface of the sapphire ring 165 and a bottom surface of the diamond electrode array 155 may both be coated with a mixture of elements such that they bond to diamond and sapphire and yield brazeable surfaces. This brazeable surface may comprise sequential metal layers of titanium, platinum and gold that may be generated using an RF bias sputtering technique with a mechanical mask or the like. In an embodiment of the present invention, the diamond electrode array 155 may be soldered onto the top surface of the sapphire ring 165. In certain aspects, the solder used to solder the diamond electrode array 155 to the top surface of the sapphire ring 165 may have a lower melting point than a braze, solder or the like used to solder/braze the sapphire ring 165 to the acoustic horn 155.

In embodiments in which the diamond electrode array 155 is soldered to the sapphire ring, the soldering may require careful positioning of the diamond electrode array 155 to provide that an electrical short circuit is not created between one or more of the conducting regions of the diamond electrode array 155 and the acoustic horn 15. In certain embodiments, a non-conducting adhesive 170 may be disposed at a gap between the diamond electrode array 155 and the acoustic horn 15. The non-conducting adhesive 170 may be a liquid non-conducting glue, such as EPO-TEC 353ND epoxy, or the like. In certain fabrication methods for some embodiments of the present invention, vacuum outgassing may be used to provide for good penetration of the non-conducting adhesive 170 into the gap prior to hardening.

In one embodiment of the present invention, electrical contact with the diamond electrode array 155 may be made using a conductive element 185. In certain aspects, the conductive element 185 may be a gold-plated pin or the like. The conductive element 185 may be disposed to provide for contact with a rear-surface of the diamond electrode array 155. In certain embodiments of the present invention, one or more non-conducting plastic members 180a and 180b may be used keep an end of the conductive element 185 in contact with the rear-surface of the diamond electrode array 155. In one embodiment, a spring 160 may be used in conjunction with the one or more non-conducting plastic members 180a and 180b to provide for keeping the conductive element 185 in contact with the rear-surface of the diamond electrode array 155. In certain aspects, the one or more non-conducting plastic members 180a and 180b may be disposed throughout the entire length of the inside of the acoustic horn 15 and electrically conducting wires, electrically conducting channels and/or the like may be disposed within the one or more non-conducting plastic members 180a and 180b to provide that an electrical short circuit does not occur.

In certain embodiments, as described in more detail with reference to FIG. 3, the conductive element 185 may comprise one or more electrically conducting elements or channels, an insulating channel-support-matrix, a mechanical support and/or the like and may be connected to a plurality of conducting wires of the like to provide for selective electrical supply to and/or selective processing of one or more of the conductive regions of the diamond electrode array 155.

In the foregoing description, for the purposes of illustration, various methods and/or procedures were described in a particular order. It should be appreciated that in alternate embodiments, the methods and/or procedures may be performed in an order different than that described. It should also be appreciated that the methods described above may be performed by hardware components and/or may be embodied in sequences of machine-executable instructions, which may be used to cause a machine, such as a general-purpose or special-purpose processor or logic circuits programmed with the instructions, to perform the methods.

Hence, while detailed descriptions of one or more embodiments of the invention have been given above, various alternatives, modifications, and equivalents will be apparent to those skilled in the art without varying the invention. Moreover, except where clearly inappropriate or otherwise expressly noted, it should be assumed that the features, devices and/or components of different embodiments may be substituted and/or combined. Thus, the above description should not be taken as limiting the scope of the invention, which is defined by the appended claims.

What is claimed is:

1. An erosion and wear resistant sonoelectrochemical probe configured for high power ultrasonic operation, comprising:
   a high power acoustic resonator, wherein the high power acoustic resonator comprises:
   an acoustic body comprising a base and a tip;
   a transducer coupled with the base and configured to vibrate the acoustic body;
   a diamond electrode coupled with the tip of the acoustic body and disposed at or proximal to a plane defined by the tip of the acoustic body; and
   an electrically conducting element or elements coupled with the diamond electrode, wherein the electrically conducting element or elements is/are electrically insulated from the acoustic body and each other; wherein the diamond electrode comprises a central disc of boron-doped diamond surrounded by a region of non-conducting diamond, and wherein the region of electrically non-conducting diamond provides for the insulation of the central disc of the boron-doped diamond from the acoustic body.

2. The sonoelectrochemical probe of claim 1 wherein the electrically non-conducting diamond comprises intrinsic diamond.

3. The sonoelectrochemical probe of claim 1, wherein the acoustic body comprises an acoustic horn.

4. The sonoelectrochemical probe of claim 3, wherein a fundamental resonant frequency of said acoustic horn is in the frequency range of 10-250 kHz.

5. The sonoelectrochemical probe of claim 3, wherein the acoustic horn comprises a substance selected from the group consisting of titanium, stainless steel and aluminum.

6. The sonoelectrochemical probe of claim 1, wherein the diamond electrode is coupled with the acoustic body by a braze or a solder.

7. The sonoelectrochemical probe of claim 1, wherein the electrically conducting element comprises a conducting wire.

8. The sonoelectrochemical probe of claim 1, wherein the electrically conducting element comprises an electrically conducting channel.

9. The sonoelectrochemical probe of claim 1, wherein the sonoelectrochemical probe is configured to function at temperatures up to at least 200 degrees Centigrade.

10. The sonoelectrochemical probe of claim 1, wherein the sonoelectrochemical probe is configured to function in fluid pressures up to at least 700 bar.

11. The sonoelectrochemical probe of claim 1, wherein the sonoelectrochemical probe is configured to function in a downhole environment.

12. The sonoelectrochemical probe of claim 1, wherein the acoustic resonator is configured to operate at sonic powers sufficient to generate acoustic cavitation in water at ambient temperature and pressure.

13. The sonoelectrochemical probe of claim 1, wherein the sonoelectrochemical probe is configured to operate under conditions where an output acoustic power generated by the acoustic resonator per unit area of the tip of the acoustic body is in excess of 0.5 W/cm$^2$.

14. The sonoelectrochemical probe of claim 1, wherein the high power acoustic resonator is configured to operate in a longitudinal mode.

15. The sonoelectrochemical probe of claim 1, wherein the diamond electrode is configured to contact a material to be electrochemically measured.

16. The sonoelectrochemical probe of claim 15, wherein the high power acoustic resonator is configured to acoustically mix the material to be electrochemically measured.

17. The sonoelectrochemical probe of claim 1, wherein the high power acoustic resonator is configured to acoustically clean the diamond electrode.

18. The sonoelectrochemical probe of claim 1, wherein the transducer comprises a piezoelectric element.

19. An erosion and wear resistant sonoelectrochemical probe configured for high power ultrasonic operation, comprising:
   a high power acoustic resonator, wherein the high power acoustic resonator comprises:
   an acoustic body comprising a base and a tip;
   a transducer coupled with the base and configured to vibrate the acoustic body;
   a diamond electrode coupled with the tip of the acoustic body and disposed at or proximal to a plane defined by the tip of the acoustic body, wherein the diamond electrode comprises a macroscopic away of electrically conducting diamond regions and electrically non-conducting diamond regions, and wherein the macroscopic array comprises a central disc of boron-doped diamond, a first plurality of concentric rings of electrically non-conducting diamond and a second plurality of concentric rings of boron-doped diamond and the first plurality of concentric rings of electrically non-conducting diamond and the second plurality of concentric rings of boron-doped diamond are arranged alternately around the central disc of boron-doped diamond; and
   an electrically conducting element or elements coupled with the diamond electrode, wherein the electrically conducting element or elements is/are electrically insulated from the acoustic body and each other.

20. The sonoelectrochemical probe of claim 19, wherein the macroscopic array of electrically conducting diamond regions and electrically non-conducting diamond regions is configured in a diamond substrate.

21. The sonoelectrochemical probe of claim 19, wherein at least one of the electrically conducting diamond regions is configured as a working electrode.

22. The sonoelectrochemical probe of claim 21, wherein at least one of the electrically conducting diamond regions is configured as a reference electrode or a counter electrode.

23. An erosion and wear resistant sonoelectrochemical probe configured for high power ultrasonic operation, comprising:
a high power acoustic resonator, wherein the high power acoustic resonator comprises:
an acoustic body comprising a base and a tip:
a transducer coupled with the base and configured to vibrate the acoustic body:
a diamond electrode coupled with the tip of the acoustic body and disposed at or proximal to a plane defined by the tip of the acoustic body, wherein the diamond electrode comprises a macroscopic away of electrically conducting diamond regions and electrically non-conducting diamond regions, and wherein the macroscopic array comprises a central disc of boron-doped diamond, a first plurality of concentric rings of electrically non-conducting diamond and a second plurality of concentric rings of boron-doped diamond and the first plurality of concentric rings of electrically non-conducting diamond and the second plurality of boron-doped diamond rings are arranged alternately around the central disc of boron-doped diamond; and
an electrically conducting element or elements coupled with the diamond electrode, wherein the electrically conducting element or elements is/are electrically insulated from the acoustic body and each other.

24. The sonoelectrochemical probe of claim 23, wherein:
the electrically conducting diamond regions comprise boron-doped diamond; and
the electrically non-conducting diamond regions comprise intrinsic diamond.

25. The sonoelectrochemical probe of claim 23, wherein the microscopic away of electrically conducting diamond regions and electrically non- conducting diamond regions are configured in a diamond substrate.

26. The sonoelectrochemical probe of claim 23, wherein the microscopic away of electrically common conducting diamond regions is configured as a working electrode.

27. The sonoelectrochemical probe of claim 23, wherein:
the central disc of boron-doped diamond is configured as a working electrode.

28. The sonoelectrochemical probe of claim 23, wherein at least one of the plurality of concentric rings of boron-doped diamond is configured as a reference electrode or a counter electrode.

29. An erosion and wear resistant sonoelectrochemical probe configured for high power ultrasonic operation, comprising:
a high power acoustic resonator, wherein the high power acoustic resonator comprises:
an acoustic horn comprising a base and a tip, wherein the acoustic horn is tapered from the base to the tip;
a transducer coupled with the base and configured to vibrate the acoustic body; and
a diamond electrode coupled with the tip of the acoustic body and disposed at or proximal to a plane defined by the tip of the acoustic body, wherein the diamond electrode comprises an array of electrically conducting diamond regions and electrically non-conducting diamond regions, and wherein the array comprises a first plurality of rings of electrically non-conducting diamond and a second plurality of rings of boron-doped diamond.

30. The sonoelectrochemical probe of claim 29, wherein the tapering of the acoustic horn comprises one of a stepwise tapering, a smooth tapering, a smooth tapering with an exponentially reducing diameter and a single step tapering such that the acoustic horn has a pin-like shape.

31. The sonoelectrochemical probe of claim 29, wherein an area of the tip of the acoustic horn is of the order of 0.2-2.0 $cm^2$.

32. The sonoelectrochemical probe of claim 29, wherein the acoustic horn is configured to operate in a longitudinal mode.

* * * * *